United States Patent [19]
Okada

[11] Patent Number: 6,152,880
[45] Date of Patent: Nov. 28, 2000

[54] SELF-DIAGNOSTIC BLOOD PRESSURE MEASURING APPARATUS

[75] Inventor: Koichi Okada, Hikone, Japan

[73] Assignee: Matsushita Electric Works, Ltd., Osaka, Japan

[21] Appl. No.: 09/273,569

[22] Filed: Mar. 22, 1999

[30] Foreign Application Priority Data

Dec. 18, 1998 [JP] Japan ................................. 10-361074

[51] Int. Cl.⁷ ........................................................ A61B 5/02
[52] U.S. Cl. ........................... 600/490; 600/485; 600/493
[58] Field of Search ................................... 600/485–504, 600/300

[56] References Cited

U.S. PATENT DOCUMENTS

| | | | |
|---|---|---|---|
| 4,245,648 | 1/1981 | Trimmer et al. | 600/502 X |
| 4,347,851 | 9/1982 | Jundanian . | |
| 4,718,427 | 1/1988 | Russell | 600/490 X |
| 4,718,891 | 1/1988 | Lipps . | |
| 4,898,180 | 2/1990 | Farretty et al. | 600/494 |
| 4,907,596 | 3/1990 | Schmid et al. . | |
| 5,298,021 | 3/1994 | Sherer . | |
| 5,836,887 | 11/1998 | Oka et al. | 600/495 X |

FOREIGN PATENT DOCUMENTS 60-132538  7/1985  Japan .

*Primary Examiner*—John P. Lacyk
*Assistant Examiner*—Ryan Carter
*Attorney, Agent, or Firm*—Arent Fox Kintner Plotkin & Kahn PLLC

[57] ABSTRACT

A self-diagnostic blood pressure measuring apparatus displays a diagnostic result for each of the measured systolic and diastolic pressures for warning to an user. The apparatus includes has a detector which measures systolic and diastolic pressures thereof, a display unit having first and second numeric indicators respectively for displaying individual numerical values of the measured systolic and diastolic pressures. A diagnosing circuit is included to compare the measured systolic and diastolic pressures respectively with predetermined systolic and diastolic reference ranges so as to provide a systolic warning when the systolic pressure is out of the systolic reference range and provide a diastolic warning when the diastolic pressure is out of the diastolic reference range. The display unit includes a warning display section which notify the systolic and diastolic warnings, individually. Thus, the systolic and diastolic warnings can be individually displayed together with the measured systolic and diastolic pressures appearing at the first and second numeric indicators, thereby providing detailed blood pressure information for immediate recognition by the user.

11 Claims, 6 Drawing Sheets

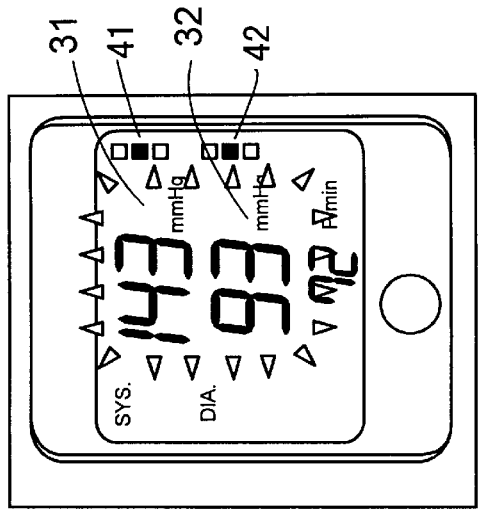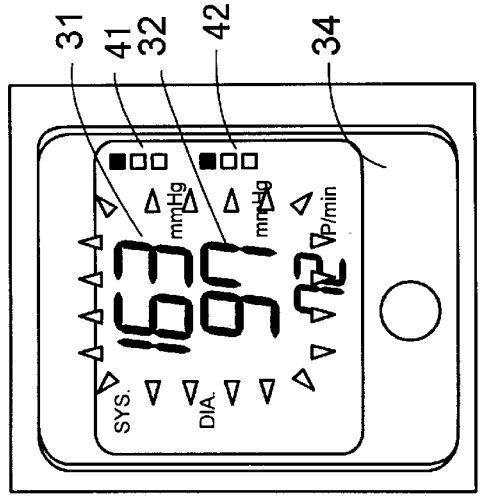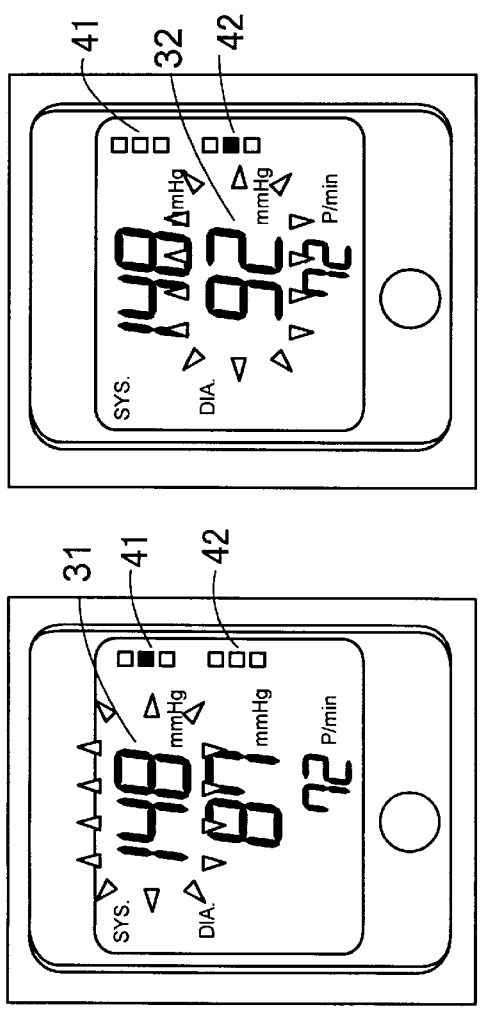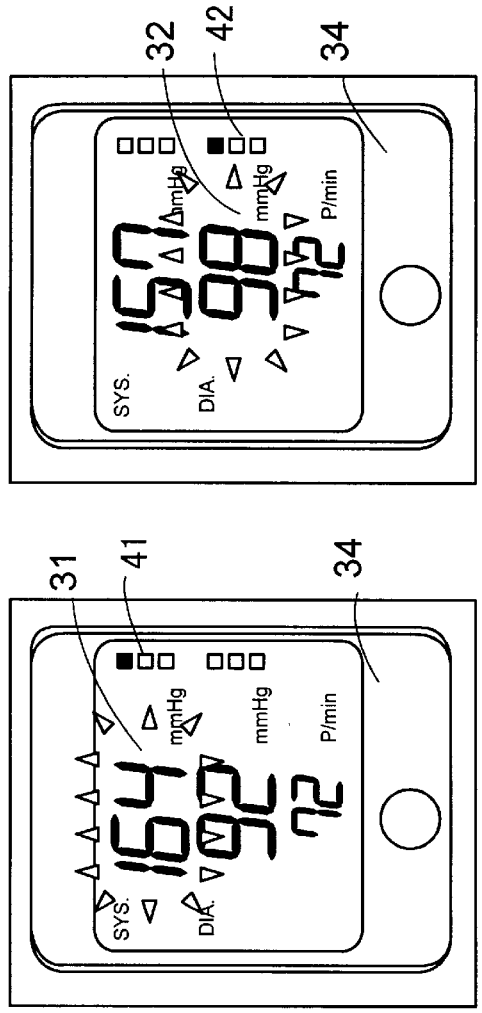

SELF-DIAGNOSTIC BLOOD PRESSURE MEASURING APPARATUS

BACKGROUND OF THE INVENTION

1. Field of the Invention

The present invention is directed to a self-diagnostic blood pressure measuring apparatus, more particularly to such apparatus which notifies an user of a blood pressure warning after displaying systolic and diastolic pressures.

2. Description of the Prior Art

Japanese Patent Publication No. 60-132538 discloses a prior blood pressure measuring apparatus which has, in addition to displaying measured systolic and diastolic pressures, a self-diagnostic function of indicating a particular blood pressure stage in which a combination of the measured systolic and diastolic pressures is classified according to regulation by World Health Organization (WHO). Thus, the user can check one's blood pressure with the help of the diagnostic result which is shown by highlighting one of zones provided in a diagnostic display. That is, the display includes three separate zones defined by systolic values and diastolic values respectively given along x-axis and y-axis to have normal blood pressure zone (where systolic pressure<140 mmHg and systolic pressure<90 mmHg), boundary line high pressure zone (where 140 mmHg≦systolic pressure<160 mmHg and 90 mmHg≦diastolic pressure<95 mmHg) and a high pressure zone (160 mmHg≦systolic pressure and diastolic pressure≧95 mmHg). However, this display is difficult to indicate direct relation between the individual blood pressures being measured and the associated zone. Particularly, when only one of the systolic and diastolic pressures is determined to be abnormal, the display is unable to give a warning by reference to the zone. Thus, the prior apparatus is found insufficient to give direct and exact blood pressure information to the user.

SUMMARY OF THE INVENTION

The present invention has been accomplished in view of the above problem to provide an improved diagnostic blood pressure measuring apparatus which is capable of displaying measured blood pressure values as well as information indicative of corresponding blood pressure zones, and therefore capable of displaying blood pressure warnings together with the measured blood pressure values even if only one of the systolic and diastolic pressures is determined to be abnormal.

The diagnostic blood pressure measuring apparatus in accordance with the present invention has a detector which is applied to a portion of a human body to measure systolic and diastolic pressures thereof, a display unit having first and second numeric indicators respectively for displaying individual numerical values of the measured systolic and diastolic pressures. A diagnosing circuit is included to compare the measured systolic and diastolic pressures respectively with predetermined systolic and diastolic reference ranges so as to provide a systolic warning when the systolic pressure is out of the systolic reference range and provide a diastolic warning when the diastolic pressure is out of the diastolic reference range. The display unit includes a warning display section which notify the systolic and diastolic warnings, individually. Thus, the systolic and diastolic warnings can be individually displayed together with the measured systolic and diastolic pressures appearing at the first and second numeric indicators, thereby providing detailed blood pressure information for immediate recognition by the user.

Preferably, the diagnosing circuit includes predetermined high systolic and diastolic reference levels which are higher than upper limits respectively of the systolic and diastolic reference ranges. Consequently, there are defined with regard to the systolic pressure, a quasi-hypertension systolic range (also referred to as a boundary line hypertension systolic range) between the upper limit of the systolic reference range and the high systolic reference level and a hypertension systolic range exceeding the high systolic reference level. Similarly, there are defined with regard to the diastolic pressure, a quasi-hypertension diastolic range (also referred to as a boundary line hypertension diastolic range) between the upper limit of the diastolic reference range and the high diastolic reference level and a hypertension diastolic range exceeding the high diastolic reference level. The diagnosing circuit compares the measured systolic and diastolic pressures respectively with the high systolic and diastolic reference levels to give 1) a low-level systolic warning when the systolic pressure is within the quasi-hypertension systolic range for notification by the warning display section;
2) a high-level systolic warning when the systolic pressure is within the hypertension systolic range for notification by the warning display section;
3) a low-level diastolic warning when the diastolic pressure is within the quasi-hypertension diastolic range for notification by the warning display section; and
4) a high-level diastolic warning when the diastolic pressure is within the hypertension diastolic range for notification by the warning display section.

With this scheme, the systolic and diastolic pressures can be individually analyzed in detail on the basis of "boundary hypertension range" and "hypertension range" defined according to the regulations of WHO.

The warning display section is preferred to include a highlighting circuit of blinking the first and second numeric indicators respectively in response to the systolic and diastolic warnings so that the blood pressure value determined to be abnormal can be immediately appealed to the eyes of the user.

In addition to or instead of the above blinking, the highlighting circuit may be arranged to change colors of the first and second numeric indicators upon receiving the warnings in order to notify the measured blood pressure value and abnormality thereof simultaneously and directly to the user.

Further, the warning display section may include first and second warning indicators which are provided separately from the first and second numerical indicators, respectively. In this instance, the first and second warning indicators are caused to turn on or blink respectively in response to the systolic and diastolic warnings for giving individual warnings to the user.

It is also desirable that the warning display section includes a highlighting circuit of blinking the first and second numerical indicators, and first and second warning indicators formed separately from the first and second numerical indicators. In this instance, the first and second warning indicators are caused to turn on or blink respectively in response to the systolic and diastol warnings, enabling to give detailed warnings. That is, the first and second numerical indicators are made to highlight the respective blood pressure values irrespective of the distinction between the high-level and low-level warnings, while the first and second warning indicators are caused to turn on or blink only in response to the high-level warnings.

Further, the warning display section may include a highlighting circuit of blinking the first and second numerical indicators, and a separately formed single warning indicator. In this instance, the single warning indicator is caused to blink only in response to the high-level systolic or high-level diastolic warnings, enabling to give distinctive identification of whether the measure blood pressure corresponds to the pseudo hypertension range (boundary line hypertension range) or hypertension range for immediate recognition by the user with a simple structure.

These and still other objects and advantageous features of the present invention will become more apparent from the following description of the embodiments when taken in conjunction with the attached drawings.

BRIEF DESCRIPTION OF THE DRAWINGS

FIG. 9, composed of FIGS. 9A to 9C, explains a warning scheme for a self-diagnostic blood pressure measuring apparatus in accordance with another embodiment of the present invention, in which FIG. 9A indicates a condition when only the systolic pressure is within the boundary line hypertension range, FIG. 9B indicates a condition when only the diastolic pressure is within the boundary line hypertension range, and FIG. 9C indicates a condition when both of the systolic and diastolic pressures are within the boundary line hypertension range; and FIG. 10, composed of FIGS. 10A to 10C, explains a warning scheme of the above apparatus, in which FIG. 10A indicates a condition when only the systolic pressure is within the hypertension range, FIG. 10B indicates a condition when only the diastolic pressure is within the hypertension range, and FIG. 10C indicates a condition when both of the systolic and diastolic pressures are within the hypertension range;

DETAILED DESCRIPTION OF THE EMBODIMENTS

First Embodiment

Figure 2:
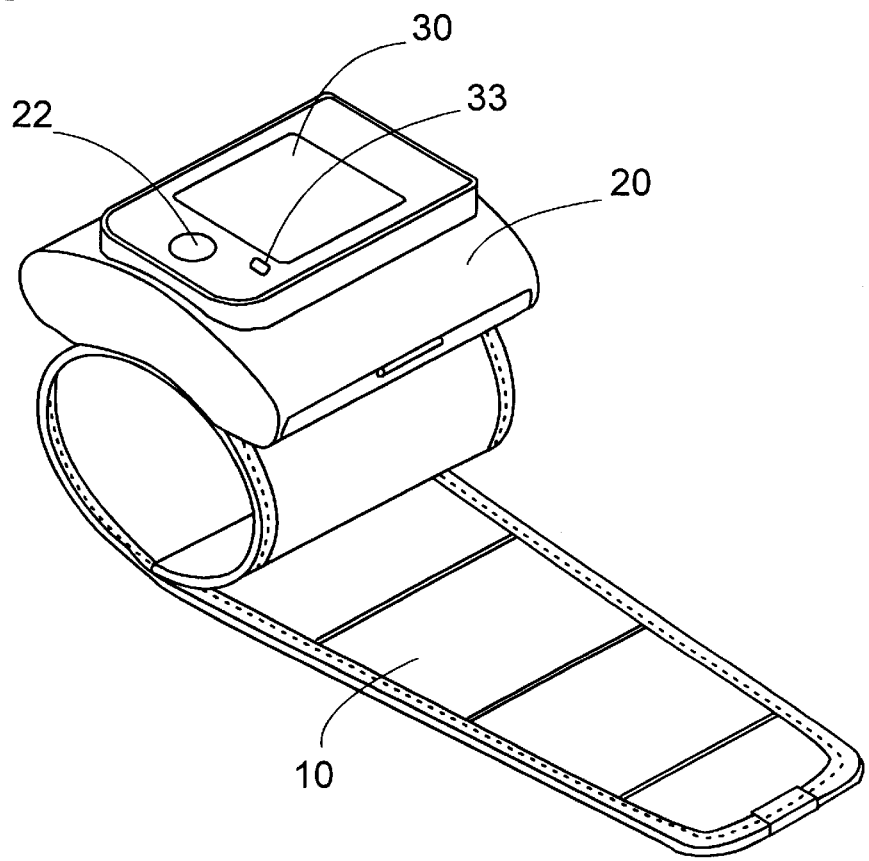
FIG. 2 is a perspective view of the above apparatus.

FIG. 2 illustrates a self-diagnostic blood pressure measuring apparatus in accordance with a preferred embodiment of the present invention. The apparatus includes an occluding cuff 10 adapted to be wound around a human's wrist, a housing 20 secured to a portion of the cuff 10. The housing 20 has a start switch 22 for starting a blood pressure measurement and a display unit for the measured results. The display unit is composed of a liquid-crystal display (LCD) 30 and a light emitting diode (LED) lamp 34. The housing 20 incorporates a pneumatic pump for inflating or collapsing the cuff 10 and an electronic circuitry for the blood pressure measurement. Mounted within the cuff 10 are a microphone for picking up the Korotocoff sound and a pressure sensor for detecting an occluding pressure. Based upon the information of the Korotocoff sound and the pressure, a blood pressure measuring circuit 50 within the housing 20 operates to measure systolic and diastolic pressures. Further, a heat rate is also measured based upon the information from the microphone.

Figure 1:
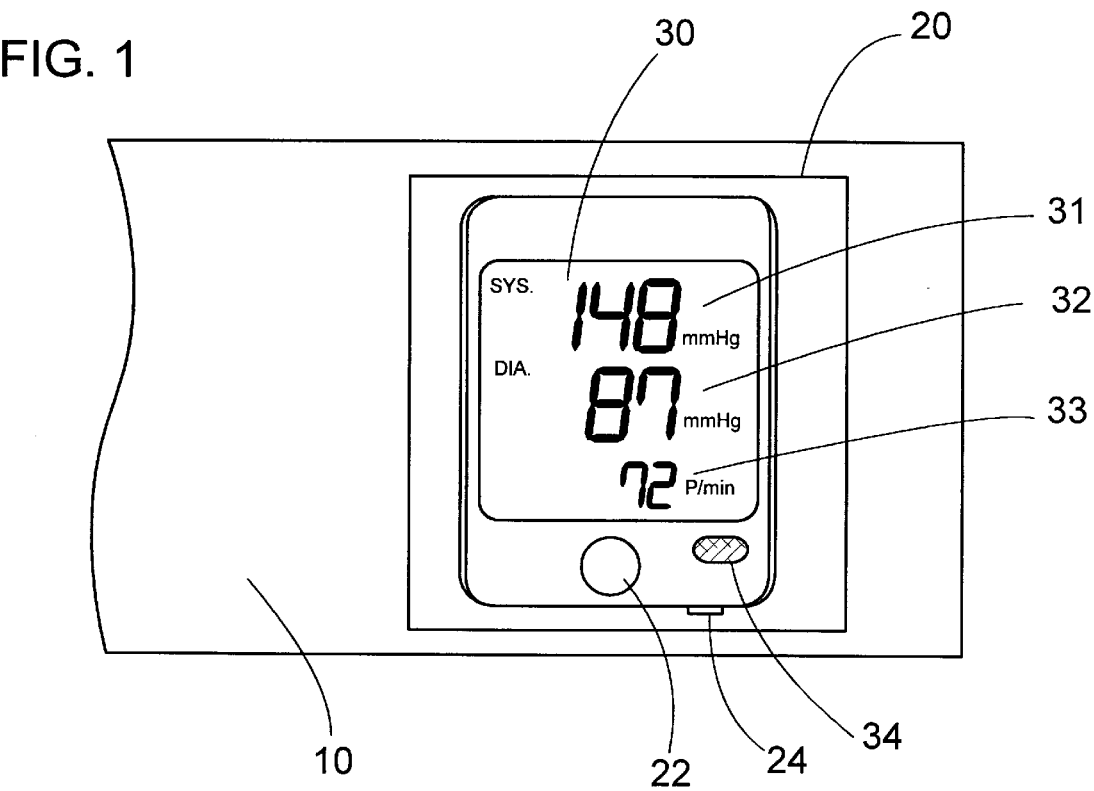
FIG. 1 is a partial plan view of a self-diagnostic blood pressure measuring apparatus in accordance with a preferred embodiment of the present invention.

As shown in FIG. 1, LCD 30 forming the display unit includes a first numerical indicator 31, a second numerical indicator 32, and a heart rate indicator 33 for indication of the measured systolic pressure, diastolic pressure and heart rate, respectively. LED lamp 34 is disposed in the top face of the housing 20 adjacent to LCD 30 for indication of a diagnostic result as explained later. The above structures are known in the art and no further explanations thereof are repeated here.

Figure 3:
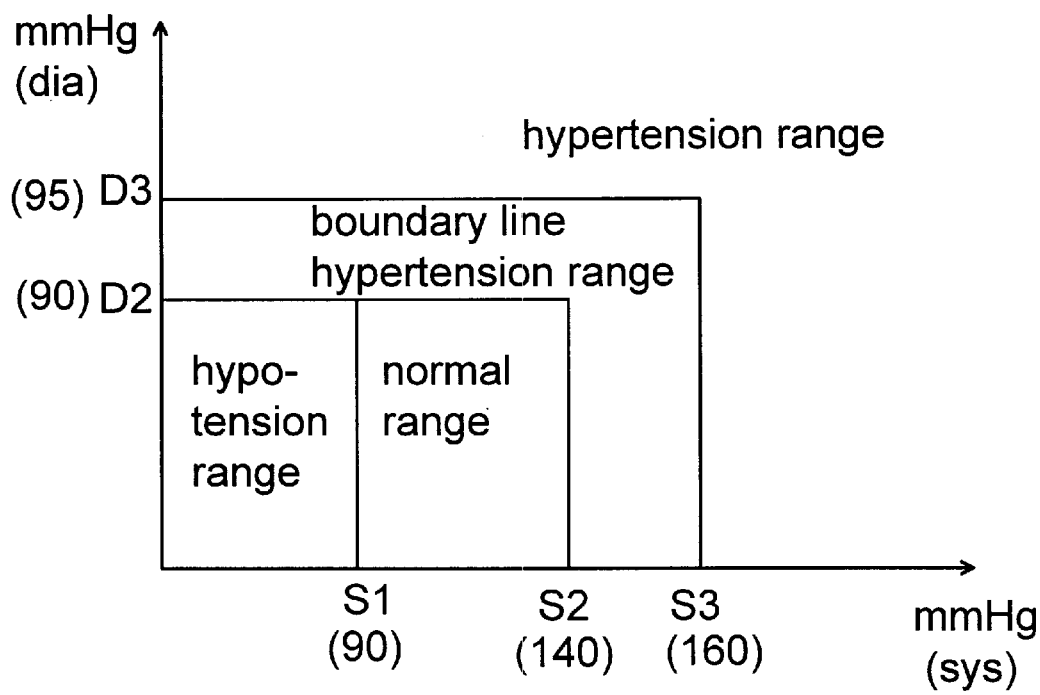
FIG. 3 is a graph showing reference levels utilized in the apparatus.
Figure 8:
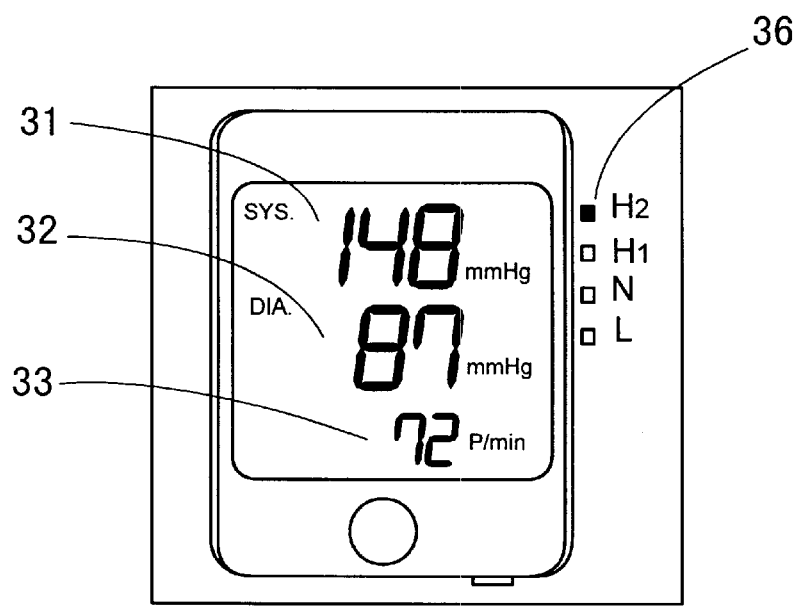
FIG. 8 is a plan view showing a display unit which may be utilized in the above apparatus.

The above electronic circuitry includes a diagnostic circuit 60 which makes a blood pressure diagnosis by comparing the measured systolic and diastolic pressures respectively with predetermined reference values which are set for each of the systolic and diastolic pressures. As shown in FIG. 3, three reference levels S1 (=90 mmHg), S2 (=140 mmHg), and S3 (=160 mmHg) are provided for the systolic pressure, and two reference levels D2 (=90 mmHg), and D3 (=95 mmHg) are provided also for the diastolic pressure. These reference values correspond to regulations specified by the World Health Organization (WHO) and therefore define a hypotension range, normal range, boundary line hypertension range, and hypertension range, as shown in the same figure.

Figure 4:
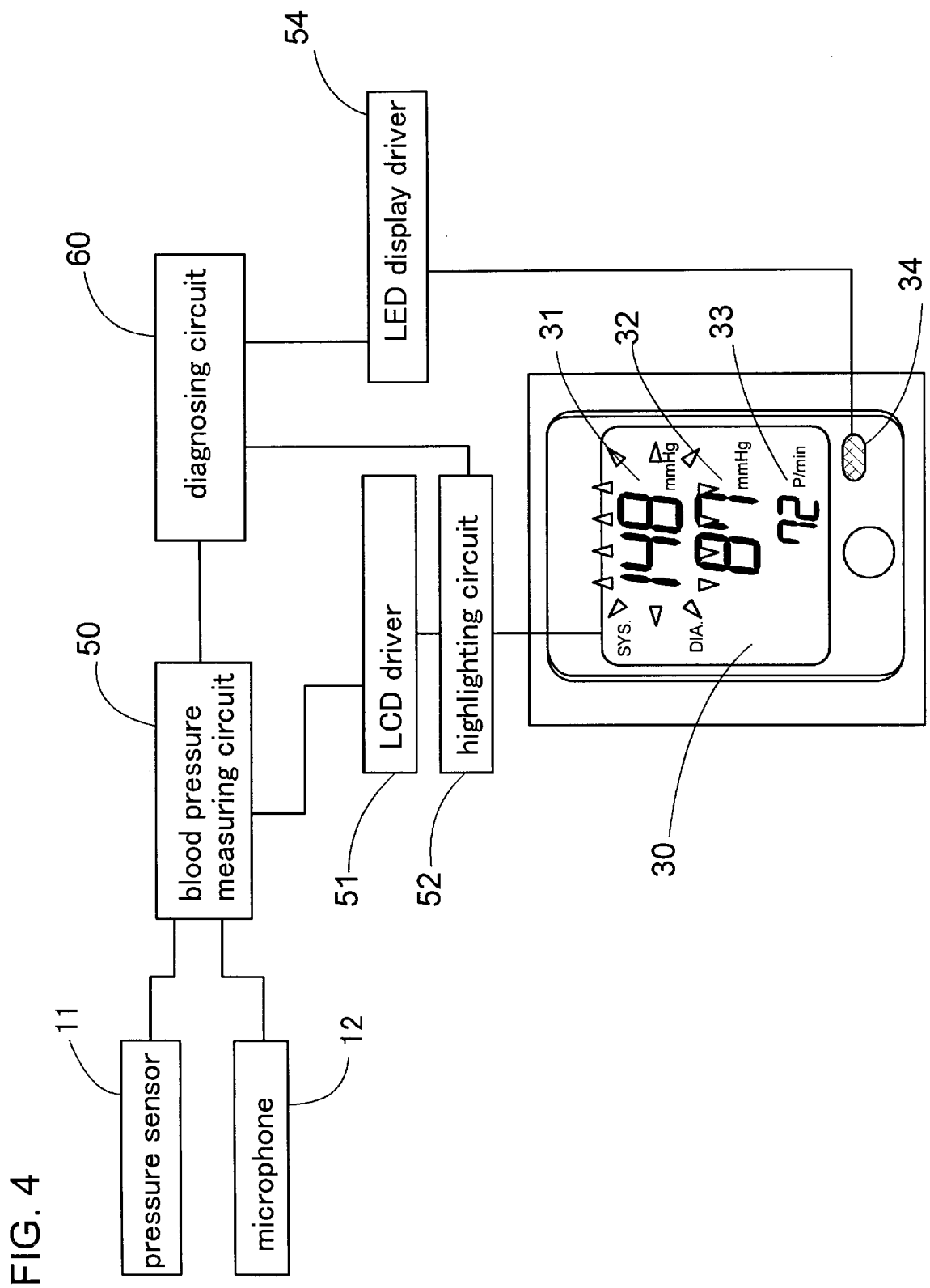
FIG. 4 is a block diagram showing a configuration of the apparatus.
Figure 5:
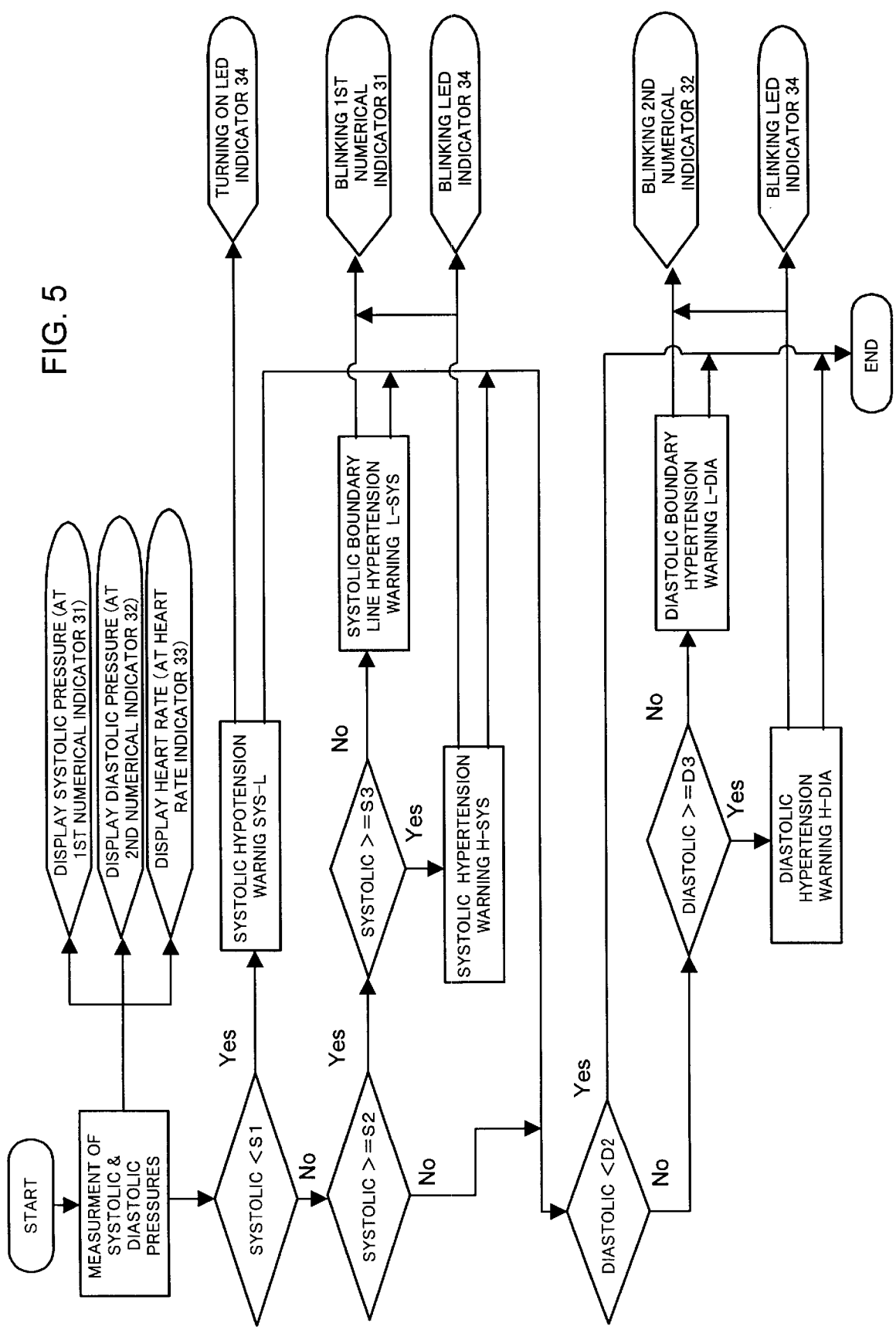
FIG. 5 is a flow chart showing the operation of the apparatus.

Operation of the blood pressure apparatus will be now discussed with reference to FIGS. 4 and 5. After winding the cuff 10 around the wrist, the start switch 22 is pressed to initiate a measurement mode in which the pneumatic pump is actuated to inflate the cuff 10 followed by discharging the air gradually from the cuff. During this cycle, pressure information from the pressure sensor 11 and the Korotocoff sound information from the microphone 12 are processed at the blood pressure measuring circuit 50 to measure the systolic pressure, the diastolic pressure, and the heart rate. Immediately thereafter, the apparatus goes into a diagnostic mode where the diagnostic circuit 60 compares the measured systolic and diastolic pressures with the above reference levels S1, S2, S3; D2, D3 in order to judge to which ranges do the systolic and diastolic pressure belong individually, and resulting warning signals to a highlighting circuit 52 and an LED display driving circuit 54. When the two measured blood pressure values exceed reference levels S2 and D2, respectively, the highlighting circuit 52 is actuated to blink the first and second numerical indicators 31 and 32. Further, when the measured blood pressure values exceed reference levels S3 and D3, the LED display driving circuit 54 is actuated to blink the LED lamp 34. Followings are examples of the operation.

Figure 6A:
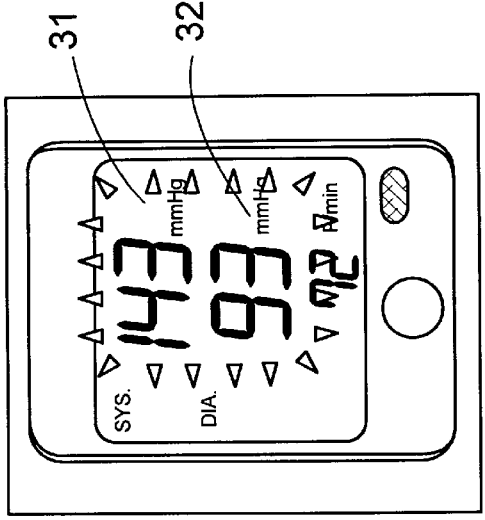
FIG. 6, composed of FIGS. 6A to 6C, explains a warning scheme, in which FIG. 6A indicates a condition when only the systolic pressure is within the boundary line hypertension range, FIG. 6B indicates a condition when only the diastolic pressure is within the boundary line hypertension range, and FIG. 6C indicates a condition when both of the systolic and diastolic pressures are within the boundary line hypertension range.

1) When S2 (=140 mmHg)≦systolic pressure<S3 (=160 mmHg), the diagnostic circuit 60 determines that the systolic pressure lies within the boundary line hypertension range to provide a low-level systolic pressure hypertension warning signal L-SYS, thereby blinking the first numerical indicator 31 displaying the systolic pressure, as shown in FIG. 6A.

Figure 6B:
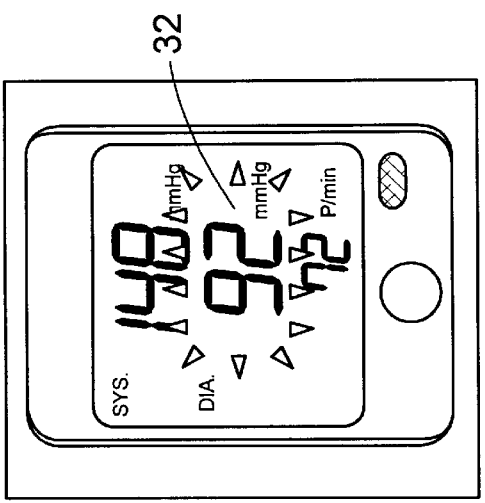

2) When D2 (=90 mmHg)≦diastolic pressure<D3 (=95 mmHg), the diagnostic circuit 60 determines that the diastolic pressure lies within the boundary line hypertension range to provide a low-level diastolic pressure hypertension warning signal L-DIA, thereby blinking the second numerical indicator 32 displaying the diastolic pressure, as shown in FIG. 6B.

Figure 6C:
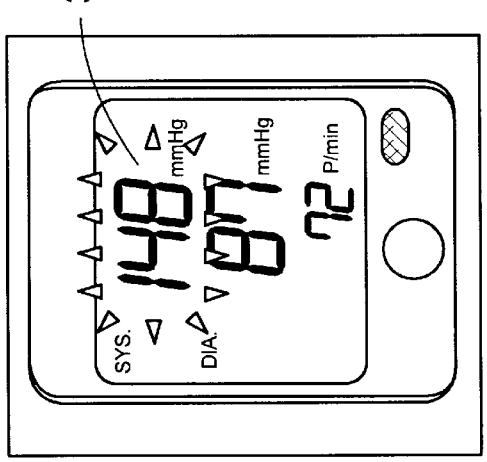

3) When the systolic and diastolic pressures are both determined to lie within the boundary line hypertension range, the diagnostic circuit 60 issues the low-level systolic and diastolic pressure hypertension warning signals L-SYS and L-DIA, thereby blinking the first and second numerical indicators 31, 32, as shown in FIG. 6C.

Figure 7A:
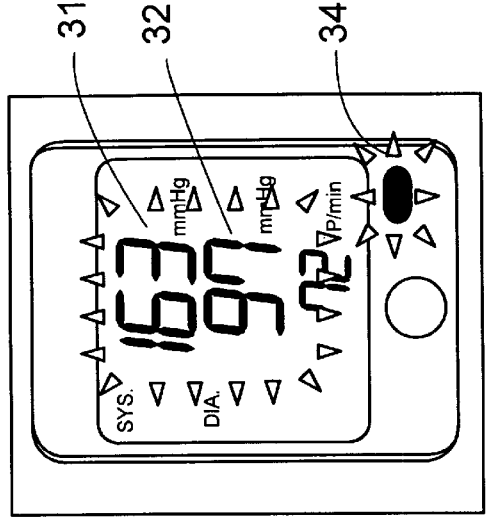
FIG. 7, composed of FIGS. 7A to 7C, explains a warning scheme, in which FIG. 7A indicates a condition when only the systolic pressure is within the hypertension range, FIG. 7B indicates a condition when only the diastolic pressure is within the hypertension range, and FIG. 7C indicates a condition when both of the systolic and diastolic pressures are within the hypertension range.

4) When the systolic pressure≧S3 (=160 mmHg), the diagnostic circuit 60 determines that the systolic pressure lies within the hypertension range to provide a high-level systolic pressure hypertension warning signal H-SYS, thereby blinking the first numerical indicator 31 displaying the systolic pressure, and at the same time blinking the LED lamp 34, as shown in FIG. 7A.

Figure 7B:
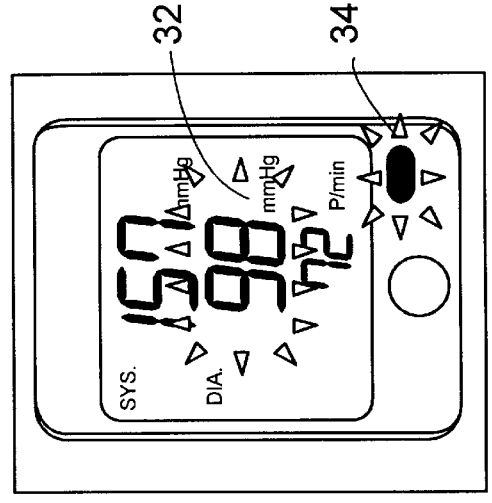

5) When the diastolic pressure≧D3 (=95 mmHg), the diagnostic circuit 60 determines that the diastolic pressure lies within the hypertension range to provide a high-level diastolic pressure hypertension warning signal H-DIA, thereby blinking the second numerical indicator 32 displaying the diastolic pressure, and at the same time blinking the LED lamp 34, as shown in FIG. 7B.

Figure 7C:
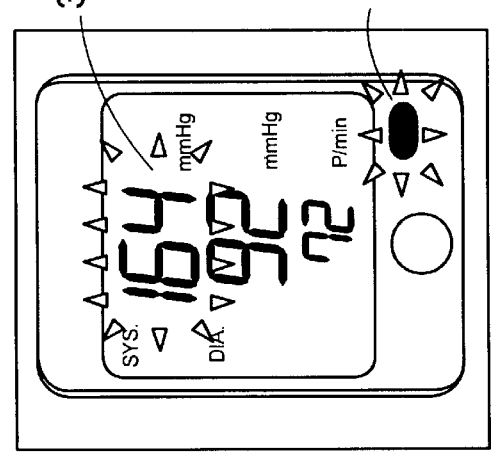

6) When the systolic and diastolic pressures are both determined to lie within the hypertension range, the diagnostic circuit 60 issues the high-level systolic and diastolic pressure hypertension warning signals H-SYS and H-DIA, thereby blinking the first and second numerical indicators 31, 32, and at the same time blinking the LED lamp 34, as shown in FIG. 7C.

In this manner, the blinking of the first and second numerical indicators 31 and 32 can notify the user that which or both of the systolic and diastolic pressures is to receive attention in direct reference to the actual blood pressure value. In addition, the blinking of LED lamp 34 can lead to easily recognition by the user of severity of the hypertension.

When both of the systolic and diastolic pressures are within the normal range, no blinking is made at the first and second numerical indicators 31, 32 and the LED lamp 34 is kept turned off, making no warning.

When the systolic pressure is determined to be less than the reference values S1, the diagnostic circuit 60 provides a systolic pressure hypotension warning signal SYS-L, causing the LED lamp 34 to turn on for displaying a hypotension warning. At this occurrence, no blinking is made at the first and second numerical indicators 31 and 32. Another reference level D1 (=60 mmHg) may be provided for the diastolic pressure which is utilized instead of D2 for comparison with the measured diastolic pressure to generate diastolic pressure hypotension warning signal DIA-L when the diastolic pressure is less than DI, causing the LED lamp 34 to turn on for displaying a hypotension warning. In this case, the diastolic pressure between D1 (=60 mmHg) and D2 (=90 mmHg) can be determined to be within a normal range.

The diagnostic blood pressure measuring apparatus of the present invention includes a diagnosis disable button 24 which is disposed on the side of the housing 20 to cancel the above diagnostic mode upon being pressed.

First Modification

In order to simplify the configuration of the blood pressure measuring apparatus, the LED lamp 34 may be eliminated so that the first and second numerical indicators 31 and 32 are caused to be highlighted by blinking when the systolic and diastolic pressures exceed S2 (=140 mmHg) and D2 (=90 mmHg), respectively for hypertension warning.

Second Modification

Although the above embodiment is contemplated to highlight the first and second numerical indicators 31 and 32, a modification may be made to highlight the indicators by changing the colors thereof, in addition to or instead of the blinking these indicators.

Third Modification

In addition to highlighting the first and second numerical indicators 31 and 32, it may be possible to express the severity of the hypertension by changing background colors of the LCD 30 rather than not relying on the LED lamp 34. For instance, the background color is changed from a normal color to a highlighted color in response to that at least one of the systolic and diastolic pressures are determined to be within the hypertension range.

Fourth Modification

Further, it is equally possible to provide a warning indicator 36 outside of LCD 30 instead of the LED lamp. The warning indicator is composed of four (4) vertically aligned lamps which corresponds to different diagnostic results and are selectively turned on according to the particular diagnostic result. That is, when either or both of the measured systolic and diastolic pressure pressures are determined to be within the hypertension range, the uppermost lamp will be turned on for warning the serious hypertension. When either or both of the systolic and diastolic pressure are determined to be within the boundary line hypertension range, the second lamp will be turned on for warning moderate hypertension. When both of the systolic and diastolic pressure is within the normal range, the third lamp will be turned on for indication of the normal condition. When either or both of the systolic and diastolic pressures are found to be within the hypotension range, the lowermost lamp will be turned on for hypotension warning. The systolic and diastolic pressures with which the warnings are made are highlighted respectively in the same manner as in the previous embodiment.

Second Embodiment

FIGS. 9 and 10 illustrate a display scheme for the self-diagnostic blood pressure measuring apparatus in accordance with a second embodiment of the present invention. The present embodiment utilizes first and second warning indicators 41 and 42 instead of the LED lamp 34. The first and second warning indicators 41 and 42 are provided within the LED 30 in proximity respectively to the first and second numerical indicators 31 and 32. The warning indicators are caused to turn on or blink in order to warn that the measured pressures are within either of the boundary line hypertension range or the hypertension range, to indicate to which range the measure pressures belong. Each of the warning-indicators is composed of three vertically aligned dots for warning based upon the diagnostic result at the diagnostic circuit. That is, the upper dot is caused to turn on or blink when either or both of the measured blood pressures are determined to be within the hypertension range. The middle dot is caused to turn on or blink when either or both of the measured blood pressures are determined to be within the boundary line hypertension range. The lower dot is caused to turn on or blink when either or both of the blood pressures are determined to be within the hypotension range.

In this manner, the diagnostic result for the measured blood pressures can be displayed at the warning indicators immediately adjacent to the numerical indicators 31 and 32.

In this instance, it is desirable to highlight the first and second numerical indicators 31 and 32, as seen in the previous embodiment. However, even without the highlighting display, the user can be easy to associate the diagnostic result at the warning indicator with the actual values at the immediately adjacent numerical indicators for recognition of the warning.

Each of the first and second warning indicator may have a single dot which is caused to turn on or blink in response to that the corresponding pressure is determined to be within the boundary hypertension range or the hypertension range.

Further, the first and second warning indicators 41 and 42 may be in the form of icons indicative of the particular warnings or windows for displaying relevant messages, instead of the dots.

It is also possible to provide, instead of the first and second warning indicators, a single warning window in the LCD 30 for displaying the warning messages determined by the diagnostic circuit, while enabling to highlight the first and second numerical indicators 31 and 32.

The above warnings can be in the form of any combination of the display schemes as described in the above, i.e., highlighting of the first and second numerical indicators, and using the dots, the icons, or the message windows. Further, it is useful to additionally provide an audible signal or voice message.

LIST OF REFERENCE NUMERALS 10 cuff
11 pressure sensor
12 microphone
20 housing
22 start switch
24 diagnosis disable button
30 LCD
31 first numerical indicator
32 second numerical indicator
33 heat rate indicator
34 LED lamp
41 first warning indicator
42 second warning indicator
50 blood pressure measuring circuit
51 LCD driving circuit
52 highlighting circuit
54 LED driving circuit
60 diagnostic circuit

What is claimed is:

1. A self-diagnostic blood pressure measuring apparatus comprising:

a detector adapted to be worn on a portion of a human body to measure diastolic and systolic pressure thereof;

a display unit secured to said detector to be portable together with said detector, said display unit having first and second numeric indicators respectively for displaying individual numerical values of said measured diastolic and systolic pressures;

a diagnosing circuit which compares said measured diastolic and systolic pressures respectively with predetermined systolic and diastolic reference ranges so as to provide a systolic warning when said systolic pressure is out of said systolic reference range and provide a diastolic warning when said diastolic pressure is out of said diastolic reference range;

said display unit including warning display means which notifies said systolic and diastolic warnings, individually.

2. The diagnostic blood pressure measuring apparatus as set forth in claim 1, wherein said diagnosing circuit includes a fixed predetermined high systolic reference level which is higher than an upper limit of said fixed systolic reference range to define a fixed quasi-hypertension systolic range between said upper limit of said systolic reference range and said high systolic reference level and a hypertension systolic range exceeding said high systolic reference level, and wherein said diagnosing circuit further includes a fixed predetermined high diastolic reference level which is higher than an upper limit of said diastolic reference range to define a fixed quasi-hypertension diastolic range between said upper limit of said diastolic reference range and said high diastolic reference level and a hypertension diastolic range exceeding said high diastolic reference level, said diagnosing circuit comparing said systolic and diastolic pressures respectively with said high systolic and diastolic reference levels to give a low level systolic warning when said systolic pressure is within said quasi-hypertension systolic range for notification by said warning display means, to give a high-level systolic warning when said systolic pressure is within said hypertension systolic range for notification by said warning display means, to give a low-level diastolic warning when said diastolic pressure is within said quasi-hypertension diastolic range for notification by said warning display means, and to give a high-level diastolic warning when said diastolic pressure is within said hypertension diastolic range for notification by said warning display means, said low-level systolic warning, said high-level systolic warning, said low-level diastolic warning, and said high-level diastolic warning giving different notifications from each other at said warning display means.

3. The diagnostic blood pressure measuring apparatus as set forth in claim 1 or 2, wherein said warning display means comprises a highlighting circuit of blinking said first and second numeric indicators, respectively in response to said systolic and diastolic warnings.

4. The diagnostic blood pressure measuring apparatus as set forth in claim 1 or 2, wherein said warning display means comprises a highlighting circuit of changing colors of said first and second numeric indicators respectively in response to said systolic and diastolic warnings.

5. The diagnostic blood pressure measuring apparatus as set forth in claims 1 or 2, wherein said warning display means include first and second warning indicators which are provided separately from said first and second numeric indicators, respectively, said first and second indicators being caused to turn on respectively in response to said systolic and diastolic warnings.

6. The diagnostic blood pressure measuring apparatus as set forth in claims 1 or 2, wherein said warning display means include first and second warning indicators which are provided separately from said first and second numeric indicators, respectively, said first and second indicators being caused to blink respectively in response to said systolic and diastolic warnings.

7. The diagnostic blood pressure measuring apparatus as set forth in claim 1 or 2, wherein said warning display means comprises a highlighting circuit of blinking said first and second numeric indicators respectively in response to said systolic and diastolic warnings, and first and second warning indicators which are caused to turn on respectively in response to said systolic and diastolic warnings.

8. The diagnostic blood pressure measuring apparatus as set forth in claim 5, wherein said first and second warning indicators (41, 42) are disposed respectively in close vicinity of said first and second numeric indicators.

9. The diagnostic blood pressure measuring apparatus as set forth in claim 2, wherein said warning display means comprises:

a highlighting circuit of blinking said first and second numeric indicators respectively in response to said high- or low-level systolic and diastolic warnings, and a single warning indicator which is caused to turn on in response to any one of said high-level systolic and diastolic warnings.

10. The diagnostic blood pressure measuring apparatus as set forth in claim 6, wherein said first and second warning indicators 41, 42 are disposed respectively in close vicinity of said first and second numeric indicators.

11. A self-diagnostic blood pressure measuring apparatus comprising:

a cuff adapted to be wound around a portion of a user;

a housing being fixed on said cuff and including a detector circuit for measuring diastolic and systolic pressures of the user;

a display unit secured on said housing to be portable together with said housing and said cuff, said display unit having first and second numeric indicators respectively for displaying individual numerical values of said measured diastolic and systolic pressures;

a diagnosing circuit which compares said measured diastolic and systolic pressures respectively with predetermined systolic and diastolic reference ranges so as to provide a systolic warning when said systolic pressure is out of said systolic reference range and provide a diastolic warning when said diastolic pressure is out of said diastolic reference range;

said display unit including warning display means which notifies said systolic and diastolic warnings, individually.

* * * * *